United States Patent
Dsinter-De Hondt et al.

(10) Patent No.: US 6,849,731 B2
(45) Date of Patent: Feb. 1, 2005

(54) PROCESS FOR RECOVERING AND PURIFYING CAPROLACTAM FROM AN ORGANIC SOLVENT

(75) Inventors: Maria Louisa Christina Dsinter-De Hondt, Genk (BE); Joannes Albertus Wilhelmus Lemmens, Roermond (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/468,263
(22) PCT Filed: Feb. 27, 2002
(86) PCT No.: PCT/NL02/00125
§ 371 (c)(1),
(2), (4) Date: Jan. 14, 2004
(87) PCT Pub. No.: WO02/070475
PCT Pub. Date: Sep. 12, 2002

(65) Prior Publication Data
US 2004/0110943 A1 Jun. 10, 2004

(30) Foreign Application Priority Data
Mar. 1, 2001 (NL) .............................. 1017471

(51) Int. Cl.$^7$ ........................................... C07D 201/16
(52) U.S. Cl. ................................................. 540/540
(58) Field of Search ........................................ 540/540

(56) References Cited

U.S. PATENT DOCUMENTS 2,758,991 A * 8/1956 Kretzers et al.
3,761,467 A * 9/1973 Williams .................... 540/540

FOREIGN PATENT DOCUMENTS

| EP | 274111 | * | 7/1988 |
| WO | 98 41502 | * | 9/1998 |
| WO | 98 49140 | * | 11/1998 |

* cited by examiner

Primary Examiner—Bruck Kifle
(74) Attorney, Agent, or Firm—Meyer, Brown, Rowe & Maw LLP

(57) ABSTRACT

Process for recovering caprolactam from a solution comprising caprolactam dissolved in an organic solvent, said process comprising:
a) washing the solution with water or an aqueous alkaline solution, resulting in a washed solution comprising caprolactam and organic solvent and in a washing residue,
b) evaporating organic solvent from the washed solution, resulting in caprolactam product,
c) optionally, hydrogenating the caprolactam product,
d) optionally, evaporating water from the caprolactam product,
e) distilling the caprolactam product to recover caprolactam and a distillation residue,
f) extracting the distillation residue with an organic solvent in the presence of water to obtain (i) an extract comprising caprolactam dissolved in organic solvent and (ii) an aqueous effluent, and
g) recycling the extract to step a) or b).

9 Claims, 1 Drawing Sheet

PROCESS FOR RECOVERING AND PURIFYING CAPROLACTAM FROM AN ORGANIC SOLVENT

CROSS REFERENCE TO RELATED APPLICATION

This application is the National Phase of International Application PCT/NL02/00125 filed Feb. 27, 2002 which designated the U.S., and that International Application was published under PCT Article 21(2) in English.

The invention relates to a process for recovering caprolactam from a solution comprising caprolactam dissolved in an organic solvent.

Such a process is for example described in WO-A-9849140. This patent publication describes that the organic phase, obtained by subjecting a neutralized rearrangement mixture of a solution of caprolactam in water and a solution of ammonium sulphate in water to extraction with benzene, is washed with (alkaline) water. Benzene is subsequently evaporated from the washed benzene solution while water is being added. Afterwards the solution of caprolactam in water is treated further. The last step is the distilling off caprolactam from water. A disadvantage of the process as described in WO-A-9849140 is that losses of caprolactam are involved.

Solutions comprising caprolactam dissolved in an organic solvent from which caprolactam is to be recovered are generally encountered in processes for the preparation of caprolactam in which cyclohexanone oxime is converted into caprolactam with the aid of an acid. This conversion is known as the Beckmann rearrangement. A base, preferably ammonia, may be added to the Beckmann rearrangement mixture, resulting in a neutralized Beckmann rearrangement mixture. The aim is to achieve the fullest possible conversion of cyclohexanone oxime into caprolactam in the rearrangement of cyclohexanone oxime as well as to isolate the caprolactam formed by the conversion of cyclohexanone oxime as fully and as purely as possible from the reaction products of the conversion in an environmentally and economically sound way.

In the recovery of caprolactam from solutions of caprolactam in an organic solvent, caprolactam losses may occur in many places. A first major cause of caprolactam losses is the occurrence of undesired side reactions of the starting materials and auxiliary materials and caprolactam with themselves or with each other, such as degradation or oligomerization. A second cause of caprolactam losses is the loss that occurs during the removal of the impurities formed by the side reactions and introduced into the process by the starting and auxiliary materials. Unstable compounds that may cause discolouration may be among such impurities. Examples of known impurities are free aldehydes or ketones and salts of metals that catalyze degradation and colour formation. Also important are the impurities that act as chain terminators, such as monofunctional acids or amines or compounds that form such substances under polymerization conditions.

The object of the present invention is to provide a process wherein the loss of caprolactam is reduced.

This object is achieved in that the process comprises
a) washing the solution with water or an aqueous alkaline solution, resulting in a washed solution comprising caprolactam and organic solvent and in a washing residue,
b) evaporating organic solvent from the washed solution, resulting in caprolactam product,
c) optionally, hydrogenating the caprolactam product,
d) optionally, evaporating water from the caprolactam product,
e) distilling the caprolactam product to recover caprolactam and a distillation residue,
f) extracting the distillation residue with an organic solvent in the presence of water to obtain (i) an extract comprising caprolactam dissolved in organic solvent and (ii) an aqueous effluent, and
g) recycling the extract to step a) or b).

BRIEF DESCRIPTION OF THE DRAWINGS

The attached FIGURE is a schematic flow diagram illustrating one embodiment of an arrangement of apparatus for carrying out an embodiment of the process according to the present invention.

It has been found that with the process of the invention the loss of caprolactam is reduced. The invention provides a process that makes it possible to treat solutions comprising caprolactam dissolved in an organic solvent in such a way that the caprolactam can efficiently be recovered from the solution. With the process of the invention caprolactam can be recovered from such a solution in sufficient purity and without significant loss of caprolactam using a minimum of energy and equipment.

Figure 1:
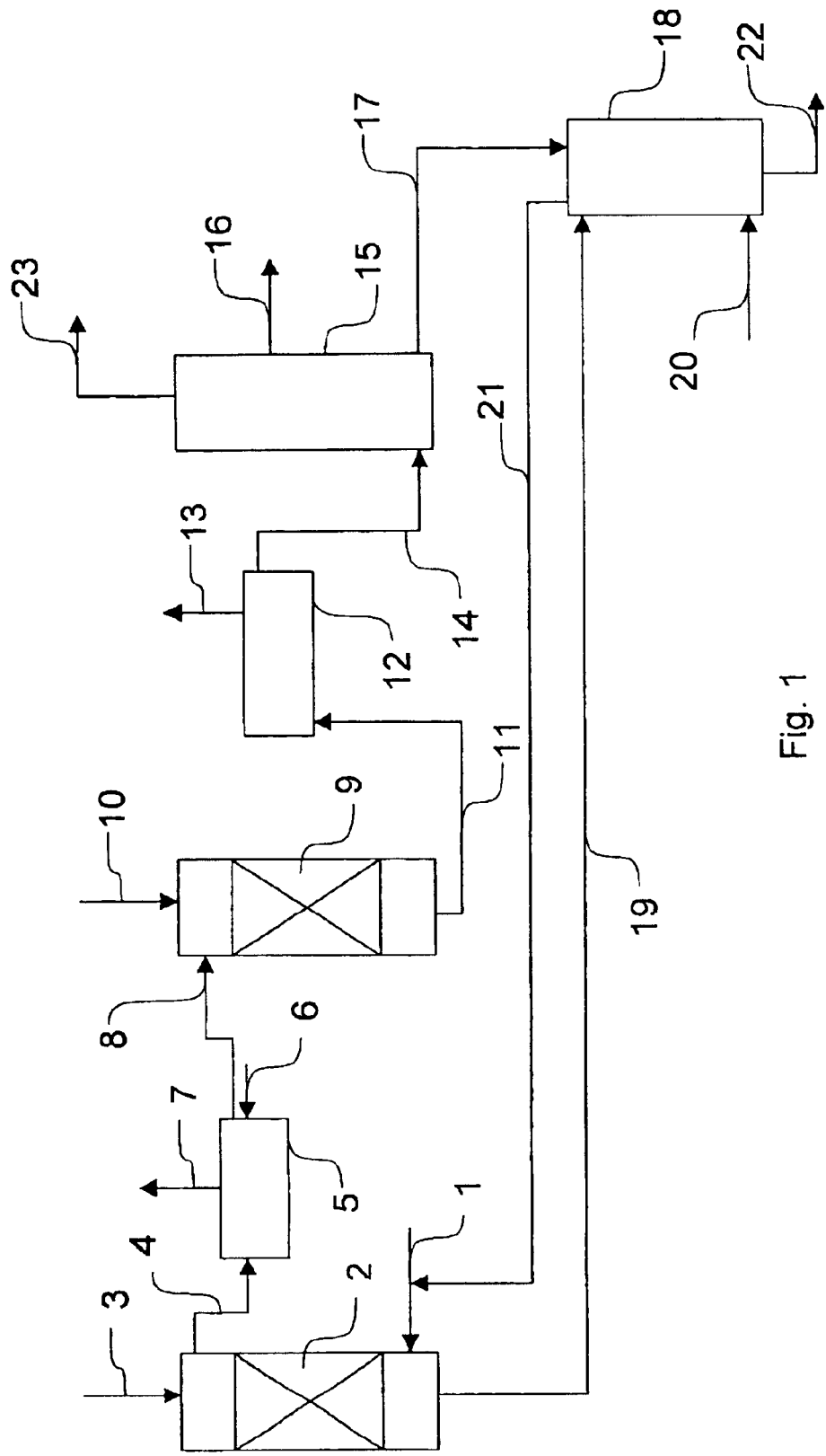

It should be remarked that between the claimed steps a)–f) other process steps may be present.

Although the concentration of caprolactam in the solution comprising caprolactam dissolved in an organic solvent is not critical, the solution generally comprises between 15 and 35 wt. %. caprolactam (relative to the total solution). Usually the solution comprises between 22 and 28 wt. % caprolactam.

The organic solvent in which caprolactam is dissolved is usually an aromatic hydrocarbon, a halogenated hydrocarbon and/or a $C_4$–$C_{10}$ aliphatic or cycloaliphatic alcohol. Examples are benzene, toluene, chloroform, trichloroethane and 4-methyl-2-pentanol. Benzene is preferred.

In step a) of the process of the invention the solution comprising caprolactam dissolved in the organic solvent is washed with water or with an aqueous alkaline solution.

If an aqueous alkaline washing is applied, as alkaline solution use can advantageously be made of a solution comprising an alkali metal hydroxide and/or alkali metal carbonate in water, preferably sodium or potassium hydroxide with a strength of 0.5–2.0 wt. %. One skilled in the art can determine the amount of water or alkaline solution with which the original solution can be washed. As a general rule, this amount is between 0.1 and 5 wt. % relative to the solution of caprolactam dissolved in organic solvent.

The water or aqueous alkaline washing can advantageously be carried out in a pulsed packed washing column, the solution (comprising caprolactam dissolved in an organic solvent) to be purified being introduced at the bottom and the water or aqueous alkaline solution at the top of the column. The (alkaline) aqueous washing results in a washed solution comprising organic solvent and caprolactam and results in a washing residue. Usually the washing residue comprises water and caprolactam. The washed solution is subsequently transported to step b) of the invention.

In step b) of the process of the invention, organic solvent is evaporated from the washed solution. Any suitable evaporation vessel may be used, for example a column. Preferably the evaporation is performed in the presence of water. More preferably the evaporation is performed as an azeotropic distillation in which case the organic solvent is evaporated as an azeotropic mixture. The evaporation results in caprolactam product. Typically the caprolactam product is an aqueous caprolactam mixture. The caprolactam content of this mixture is usually between 85 and 99.9 wt. % relative to the entire stream.

The caprolactam product obtained in step b) is optionally, but preferably hydrogenated in the presence of a hydrogenation catalyst known per se. The hydrogenation can advantageously be carried out as for example described in EP-A-635487.

Optionally water is evaporated from the, optionally hydrogenated, caprolactam product. Preferably, water is evaporated from the, optionally hydrogenated, caprolactam product. Following the hydrogenation and/or evaporation of water, the caprolactam product is distilled to recover caprolactam product and a distillation residue. Preferably, the distilling is carried out at reduced pressure. Preferably the distillation is effected at a pressure of less than 50 kPa, more preferably less than 20 kPa, in particular less than 10 kPa. Preferably, the temperature is between 100 and 200° C., more preferably between 110 and 180° C. These temperatures refer to the temperature in the bottom of the distillation column in which the distillation is effected. Typically, the distilling includes separating low-boiling organic impurities (having a lower boiling point than caprolactam) from the caprolactam product and/or separating organic high-boiling impurities (having a higher boiling point than caprolactam) from the caprolactam product. Usually, the distilling includes, in a first step, separating out as a top product low-boiling impurities from the caprolactam product while leaving caprolactam product containing high-boiling impurities as a bottom product, and, in a second step, separating out as a top product purified caprolactam while leaving as a bottom product a distillation residue comprising caprolactam and high boiling impurities.

The distillation residue is extracted in step f) of the process of the invention with an organic solvent in the presence of water to obtain (i) an extract comprising caprolactam dissolved in organic solvent and (ii) an aqueous effluent containing impurities. Although the concentration of caprolactam and of the impurities is not critical, the distillation residue generally comprises between 80 and 99.5 wt. % caprolactam and between 0.5 and 20 wt. % impurities. Usually the concentration of impurities lies between 1 and 5 wt. % (relative to the amount of caprolactam).

The extraction f) is usually performed at a moderate temperature, generally between 20 and 60° C. It has been found that the use of extraction instead of a distillative fine purification under vacuum at a temperature that is relatively high, as a rule higher than 100° C., most surprisingly enables good and equipment-wise simple recovery of caprolactam. A further advantage of an extraction over a distillation is that formation of side products and caprolactam losses, such as occur under the conditions of a residue distillation, are prevented. This results in an improvement in the quality of the caprolactam, while in addition the caprolactam yield can be increased.

The pressure of the extraction f) is not critical and may be between 0.1 and 1 MPa.

The extraction f) is performed using an organic solvent in the presence of water. As organic solvents use may be made of aromatic hydrocarbons, halogenated hydrocarbons and/or $C_4$–$C_{10}$ aliphatic or cycloaliphatic alcohols. Examples are benzene, toluene, chloroform, trichloroethane and 4-methyl-2-pentanol. Benzene is preferred. Preferably the organic solvent of the original solution and the organic solvent for the extraction are the same. One skilled in the art can easily determine the optimal amount of organic solvent and of water. It has been found that performing the extraction in the presence of alkali, the extraction efficiency is further improved. For example, smaller extraction equipment can be used and/or the amount of impurities in the extract can be lowered when performing the extraction in the presence of alkali. It is preferred that the amount of alkali is not too high since we found that the presence of alkali may result in degradation of caprolactam. The skilled person can determine the optimum amount of alkali. Preferably, the extraction f) is performed in the presence of between 0.001 and 5 wt. % alkali, more preferably between 0.001 and 2 wt. % (relative to the original solution comprising caprolactam dissolved in organic solvent). Preferably sodium or potassium hydroxide is used as alkali.

The extraction f) results in an extract comprising caprolactam dissolved in organic solvent and an aqueous effluent mainly containing impurities and only very little caprolactam. The aqueous effluent may for example be subjected to a biopurification.

The extraction f) can be carried out in the usual liquid—liquid contactors, for example mixer-setllers, pulsed packed columns or rotating disc columns. The extraction is preferably performed in a counter currently operated vertically placed vessel, wherein to the top of the vessel the distillation residue to be extracted is fed and to the bottom the organic solvent and optionally water. In this case, the extract and the aqueous effluent are obtained at the top and bottom of the column respectively.

In the process of the invention, the extract is recycled to step a) or b). In a preferred embodiment of the invention, the extract is recycled to a) because this improves the purification.

In a more preferred embodiment of the invention, the washing residue and the distillation residue are jointly extracted in f). It has been found that in this embodiment of the invention the loss of caprolactam is further reduced. Advanteously, the washing and distillation residue are first mixed and the so obtained mixture is extracted. This embodiment of the invention is advantageous because no two separate after-treatments are required, so that the equipment costs can be strongly reduced and the process is also rendered less susceptible to upsets.

In an even more preferred embodiment of the invention, the washing residue and the distillation residue are jointly extracted in f) and the so-obtained extract is recycled to step a). It has surprisingly been found that this embodiment of the invention yields an extract that can be fed to the water or alkaline washing column without loss or substantial loss of quality of the ultimate obtained caprolactam. This is especially surprising since the extraction f) is performed with the same solvent as the washing a). This means that impurities that enter into the solution comprising caprolactam and organic solvent during the washing (the washing solution) do not enter the solution comprising caprolactam dissolved in organic solvent (the extract) during the extraction, although the conditions in the washing and extraction equipment (concentration and solvent) are comparable. An accumulation of impurities, which could result in foaming during the washing operation, was indeed never observed.

The process according to the invention is especially suitable for being carried out in combination with a known cyclohexanone oxime preparation in which no or relatively few impurities are formed and/or in general in those cases in which extra measures have been taken that result in a lower impurity content of the solutions to be purified. Thus, the process according to the invention can advantageously be used in combination with the preparation of cyclohexanone oxime according to the HPO process (Ullmann's Encyclopedia of Industrial Chemistry, 1986, Vol A5, p. 35).

The invention will below be elucidated with reference to the schematic drawing shown in the Figure and by an example, without being limited hereto.

In the FIGURE a solution of caprolactam dissolved in benzene with a caprolactam content of 15–30 wt. % is fed through feed line 1 to the bottom of an alkaline washing column 2, which may for instance be designed as a pulsed column. At the top of alkaline washing column 2 an aqueous 0.5–2.0 wt. % alkaline solution is introduced into the washing column through line 3, which solution in terms of weight corresponds to 0.1–5.0 wt. % of the benzene feed. Line 4 transports the washed solution comprising caprolactam and benzene to benzene evaporation equipment 5. Benzene evaporation is effected by means of an azeotropic distillation with water being supplied through line 6. Benzene leaves the evaporator through line 7. The caprolactam transferred to water, so-called caprolactam product with a caprolactam concentration of about 93–99 wt. %, is if desired transported through line 8 to a hydrogenation column 9, to which hydrogen is supplied through line 10. The hydrogenation is optional. After this, the (optionally hydrogenated) caprolactam product is fed through line 11 to final water evaporator 12 to be dewatered. The evaporated water escapes through line 13 while the caprolactam product, now evaporated to about 99.5 wt. % caprolactam, is fed through line 14 to fractionated vacuum distillation equipment 15. Purified caprolactam is discharged through 16 to be stored. Through line 17 the distillation residue from distillation equipment 15 is fed to an extraction column 18, which also receives the washing residue from alkaline washing column 2 through line 19. These two process streams are subjected to a extraction with benzene in column 18. The benzene is supplied through line 20. The caprolactam extracted from the two process streams by the benzene, the so-called extract, is returned through line 21 as a benzene stream containing about 10–25 wt. % caprolactam to feed line 1 at the bottom of alkaline washing column 2. An effluent containing many impurities and still only very little caprolactam is subjected to for instance a biopurification via line 22. If this is advantageous, water discharged through line 13 can be fed to the extraction. The low boiling impurities from distillation equipment 15 is discharged through line 23. In practice, the distillation equipment denoted by 15 often consists of two or three columns.

In all examples the specifications given were determined using the following ISO standards:
PAN: ISO DIS 8660—Plastics—Determination of permanganate index of caprolactam—Spectrometric method, revision of first edition (ISO 8660: 1988). Voting started on 2000 Apr. 20, voting terminated on 2000 Sep. 20
E290: ISO 7059—Caprolactam for industrial use—
Determination of absorbance at a wave length of 290 nm.
First edition—1982 Dec. 1 (Ref. No. ISO 7059–1982(E)
Volatile bases (VB) ISO 8112—Caprolactam for industrial use—Determination of colour of 50% aqueous caprolactam solution, expressed in Hazen units (platinum cobalt scale)—Spectrometric method.
First edition—1984 Nov. 15 (Ref. No. ISO 8112-1984(E)

EXAMPLE I

Crude caprolactam obtained in a Beckmann rearrangement is, after neutralization, extracted with benzene in the customary manner, so that a solution of 20 wt. % caprolactam dissolved in benzene is formed. Of this solution, the so-called benzenic caprolactam, 310 l/h is fed to the bottom of a pulsed washing column. The washing column has a diameter of 10 cm, a height of 5 m and is filled with 2.5 cm packing rings. Via the top of the washing column 3.4 l/h water with 1.0 wt. % NaOH is supplied. The temperature in the washing column is 40° C. At the top of the washing column the washed benzenic caprolactam is drained while a water/caprolactam mixture with 46 wt. % caprolactam and 0.06 wt. % NaOH leaves the bottom of the washing column as the washing residue.

The above-mentioned washed benzenic caprolactam is freed of benzene by means of an azeotropic distillation with water addition and then hydrogenated. The process stream leaving the hydrogenation, still containing water, is subsequently, as main stream, to a large extent freed of water and fed to a continuous final distillation at a pressure of 1–1.5 kPa in a distillation column with a structured packing height of 1 m. The division or split is set such that 10 wt. % of the feed leaves the distillation column as bottom stream, the distillation residue. The purified caprolactam leaving the distillation column, hereinafter referred to as final caprolactam product, has the following properties: PAN=2.2; E290= 0.06; Colour=1.

Equal amounts by weight of washing residue and distillation residue are combined into an aqueous caprolactam mixture containing 72.1 wt. % caprolactam, water and still 2.2 wt. % impurities such as for instance aminocaproic acids, carboxylic acids and sulfonic acids. This mixture, hereinafter referred to as final residue, undergoes a further treatment for the recovery of the caprolactam contained in it.

Of the final residue 40 l/h is fed to the top of a 5 m high pulsed extraction column with a diameter of 10 cm and provided with 2.5 cm packing rings. To the bottom 140 l/h benzene is fed. The extraction temperature is 40° C. The benzene/caprolactam stream leaving the top of the column contains 19.1 wt. % caprolactam. This process stream is used as approx. 15 wt. % replacement of the benzenic caprolactam fed to the alkaline washing column and then passes through all previously described operations. The purified caprolactam leaving the distillation column, the final caprolactam product, now has the following properties: PAN=2.2; E290=0.06; Colour=1.

COMPARATIVE EXAMPLE A

Instead of recovery of the caprolactam from the final residue using extraction as described in Example I, the final residue is now treated further using distillation techniques. In a batch distillation first the water is removed, the pressure constantly being reduced so that the bottom temperature does not rise above 130° C. At 1.5 kPa, when the bottom temperature threatens to rise to above 130° C., the batch distillation is stopped; the resulting caprolactam is now cooled to 80° C. and fed to a continuous distillation column provided with a 1 m high structured packing. The column operates at a pressure of 1.5 kPa. For the supply of heat use is made of a film evaporator. The bottom temperature is 130° C. It is found that, due to the increase in the viscosity, as a result of which the heat supply to the mass becomes insufficient, the distillate amounts to at most 66 wt. % of the feed. In line with the ratio in large-scale technical operations, 15 parts by weight of this caprolactam distillate are mixed with 85 parts by weight of the purified caprolactam from the main stream, as described above under Example I. The final caprolactam product then has the following properties:
PAN=5; E290=0.25; Colour=2.

Examination of the properties of the final caprolactam products of Example I and those of Comparative Example A shows that the final caprolactam product obtained with the process according to the invention yields properties that are superior to those as obtained in Comparative Example A.

What is claimed is:
1. Process for recovering caprolactam from a solution comprising caprolactam dissolved in an organic solvent, said process comprising:
   a) washing the solution with water or an aqueous alkaline solution, resulting in a washed solution comprising caprolactam and organic solvent and in a washing residue,
   b) evaporating organic solvent from the washed solution, resulting in caprolactam product, c) optionally, hydrogenating the caprolactam product, d) optionally, evaporating water from the caprolactam product, e) distilling the caprolactam product to recover purified caprolactam as a top product and a distillation residue as a bottom product comprising caprolactam and impurities, f) extracting the distillation residue with an organic solvent in the presence of water to obtain (i) an extract comprising caprolactam dissolved in organic solvent and (ii) an aqueous effluent, and g) recycling the extract to step a) or b).

2. Process according to claim 1, wherein said extracting is performed in the presence of alkali.

3. Process according to claim 1, wherein the extract is recycled to step a).

4. Process according to claim 1, wherein in step f) the distillation residue and the washing residue are jointly extracted.

5. Process according to claim 1, wherein the organic solvent for the caprolactam is the same as the organic solvent for extracting the residue(s).

6. Process according to claim 5, wherein the organic solvent is benzene.

7. Process according to claim 1, wherein the washing takes place in a pulsed packed washing column.

8. Process according to claim 1, wherein in step b) the organic solvent is evaporated as an azeotropic mixture.

9. Process according to claim 1, wherein the caprolactam has been obtained by a Beckmann rearrangement of cyclohexanone oxime.

* * * * *

UNITED STATES PATENT AND TRADEMARK OFFICE
CERTIFICATE OF CORRECTION

PATENT NO. : 6,849,731 B2
DATED : February 1, 2005
INVENTOR(S) : Dsinter-De-Hondt et al.

It is certified that error appears in the above-identified patent and that said Letters Patent is hereby corrected as shown below:

<u>Title page,</u>
Item [75], Inventors, add -- Louise Annemarie Groot Zevert --

Signed and Sealed this

Second Day of August, 2005

JON W. DUDAS
*Director of the United States Patent and Trademark Office*